(12) United States Patent
Praetzel

(10) Patent No.: US 7,935,858 B2
(45) Date of Patent: May 3, 2011

(54) TISSUE SPACER FOR WOUND TREATMENT EMPLOYING REDUCED PRESSURE AND METHOD AND APPARATUS EMPLOYING SAME

(76) Inventor: Daron Carl Praetzel, Centerville, OH (US)

( * ) Notice: Subject to any disclaimer, the term of this patent is extended or adjusted under 35 U.S.C. 154(b) by 124 days.

(21) Appl. No.: 12/193,539

(22) Filed: Aug. 18, 2008

(65) Prior Publication Data

US 2010/0042033 A1 Feb. 18, 2010

(51) Int. Cl.
*A61F 13/00* (2006.01)
*A61F 5/44* (2006.01)
(52) U.S. Cl. .................. 602/43; 128/888; 604/328
(58) Field of Classification Search ............. 602/41–43; 128/898, 888; 424/443–449, 210; 601/6, 601/11; 604/543, 327, 328, 317, 313, 9, 332, 335
See application file for complete search history.

(56) References Cited

U.S. PATENT DOCUMENTS

| | | | | |
|---|---|---|---|---|
| 5,636,643 A | * | 6/1997 | Argenta et al. | 128/897 |
| 5,645,081 A | | 7/1997 | Argenta et al. | |
| 5,755,769 A | * | 5/1998 | Richard et al. | 623/1.2 |
| 6,695,823 B1 | | 2/2004 | Lina et al. | |
| 7,569,742 B2 | * | 8/2009 | Haggstrom et al. | 602/53 |
| 2002/0156437 A1 | | 10/2002 | McDevitt et al. | |
| 2003/0225347 A1 | | 12/2003 | Argenta et al. | |
| 2004/0064111 A1 | | 4/2004 | Lockwood et al. | |

* cited by examiner

*Primary Examiner* — Patricia M Bianco
*Assistant Examiner* — Ophelia Hawthorne
(74) *Attorney, Agent, or Firm* — R. William Graham

(57) ABSTRACT

A tissue spacer shaped to a general configuration of a projected tissue growth site of a patient for use in conjunction with vacuum suction for medical purposes and reduced pressure device and method employing the same.

7 Claims, 2 Drawing Sheets

TISSUE SPACER FOR WOUND TREATMENT EMPLOYING REDUCED PRESSURE AND METHOD AND APPARATUS EMPLOYING SAME

FIELD OF THE INVENTION

The present invention relates to wound treatment. More particularly, but not by way of limitation, the invention relates to a tissue spacer for use in treating a wound in a reduced pressure apparatus and method and apparatus employing the spacer.

BACKGROUND OF THE INVENTION

Current treatment of open wounds that are large and difficult to quickly close has not met with acceptable results. A current technique is to provide an impermeable cover adapted to cover and enclose the wound and adapted to maintain reduced pressure at the site of the wound. A seal is adapted to seal the cover to tissue surrounding the wound. A vacuum cooperates with the cover to supply reduced pressure beneath the cover and a rigid screen is provided which meets the seal surrounding the wound and is adapted to prevent overgrowth of wound tissue, the screen being located between the wound and the cover. This type of closure of an open wound provided some advancement in the art in addressing large wounds which are not able to heal spontaneously and are unable to successfully fight bacterial infection.

The current technology is effective in surrounding the tissue and providing an environment in which an initial stage of wound healing can occur which is characterized by the formation of granulation tissue which is a matrix of collagen, fibronectin, and hyaluronic acid carrying macrophages, fibroblasts, and neovasculature that forms the basis for subsequent epithelialization of the wound. This technique aided in increasing blood circulation within wounded tissue to promote healing and reduce infection and aided skin grafts and flaps.

Grafts and flaps can be used with much greater success on tissue that, although wounded, is able to form granulation tissue. Enhancing the technique for promoting blood circulation at the wounded tissue would also promote successful attachment, or "take," of skin grafts or flaps to the wounded tissue as a consequence of increased blood circulation within the grafts or flaps.

However, this closure mechanism does not provide a mechanism for sufficiently repairing the tissue to an acceptable aesthetic configuration. Typically, the repair leaves the tissue permanently disfigured from its original shape. For example, in the case of burn victim's facial tissue being partially gone, the current technique provided suction using a flat surface which left the patient's tissue substantially disfigured.

Accordingly, there is a need to improve on the art in the field of negative pressure wound healing. There is also a need for providing a wound healing device which enables improved tissue growth configuration.

SUMMARY OF THE INVENTION

It is an object to improve wound healing.
It is another object to improve methods for treating wounds through negative pressure.
It is a further object to improve the apparatus for healing wounds.

It is another object to improve tissue spacers for use in wound healing.

In accordance with the present invention there is provided a tissue spacer readily shaped to a general configuration of a projected tissue growth site of a patient for use in conjunction with vacuum suction for medical purposes. The spacer has a shaped member with perforations therethrough and having an outer surface configured to take a shape of a projected outer surface tissue which spans and connects surrounding normal tissue of the patient and further characterized to include a contour complementary to the patient's surrounding normal tissue and the shaped member having a peripheral edge extending laterally from the outer surface which is of a length configured to lay below the surrounding normal tissue.

The instant invention calls for a tissue spacer including a shaped member having perforations therethrough and having an outer surface which generally confines and surrounds about but does not substantially occupy a void of a wound which is surrounded by generally normal dermis tissue of a patient and is configured to take a shape of a projected outer surface tissue which spans and connects surrounding generally normal dermis tissue of the patient and further characterized to include a contour complementary to the patient's surrounding generally normal dermis tissue and the shaped member having a peripheral edge extending laterally from the outer surface which is of a length configured to lay below the surrounding generally normal dermis tissue. Further, a reduced pressure supply device is equipped for creating a pressure differential through the tissue spacer in a manner such that when the tissue spacer is disposed on the patient the device causes growth of tissue in a manner to conform with the shape of the contour of the tissue spacer and fill the void over time.

The shape allows a volume potential such that when a reduced pressure is applied tissue of the wound fills the prior void. The intent of the spacer is to allow the tissue to fill the void of the missing tissue so that tissue regeneration and granulation is improved at the wound site.

Reduced pressure (i.e. pressure that is below ambient atmospheric pressure via a vacuum) to the wound is applied in a controlled manner for a selected time period over the spacer. The application of reduced pressure to a wound through the improved spacer provides exceptional formation of granulation tissue, wound healing and closure as well as reduced bacteria growth and enhanced grafting.

The wound treatment apparatus in accordance with the present invention for use in treating patients requiring a projected tissue growth volume within an exposed wound site in order to form a predetermined physical configuration including a tissue spacer having an outer surface and lateral edge generally configured to lay within the wound wherein the outer surface serves as a boundary for the projected tissue growth volume. A reduced pressure application appliance is applied about the spacer in a manner to create a vacuum to thereby promote vascular growth and tissue granulation.

Additionally, a porous sponge or open cell foam material can preferably be applied over the spacer. The sponge would thus prevent or limit growth of the tissue growth about the spacer in a manner which would hinder removal of the spacer.

A computer based device can be operably connected to the reduced pressure device for controlling pressure differential to the tissue growth site. A sensor can be operably disposed adjacent the tissue growth site for sensing a condition thereof and operably connected to the computer based device such that the computer based device controls the reduced pressure device as a function of the condition. Artificial intelligence can be employed to perform the control of reduced pressure device.

A method of administering a reduced pressure treatment to a projected tissue growth site of a patient includes the steps of (a) disposing a tissue spacer onto a patient at the projected tissue growth site wherein the tissue spacer includes a shaped member having perforations therethrough and having an outer surface configured to take a shape of a projected outer surface tissue which spans and connects surrounding normal tissue of the patient and further characterized to include a contour complementary to the patient's surrounding normal tissue and the shaped member having a peripheral edge extending laterally from the outer surface which is of a length configured to lay below the surrounding normal tissue and creating a pressure differential through the tissue spacer in a manner such that when the tissue spacer is disposed on the patient the pressure differential causes growth of tissue in a manner to conform with the shape of the contour of the tissue spacer. The method further includes forming a tissue spacer to a general configuration of a wound, disposing the spacer within the wound and employing a vacuum in a manner to create a negative pressure through the spacer to cause tissue granulation and promote healing.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENTS

Figure 1:
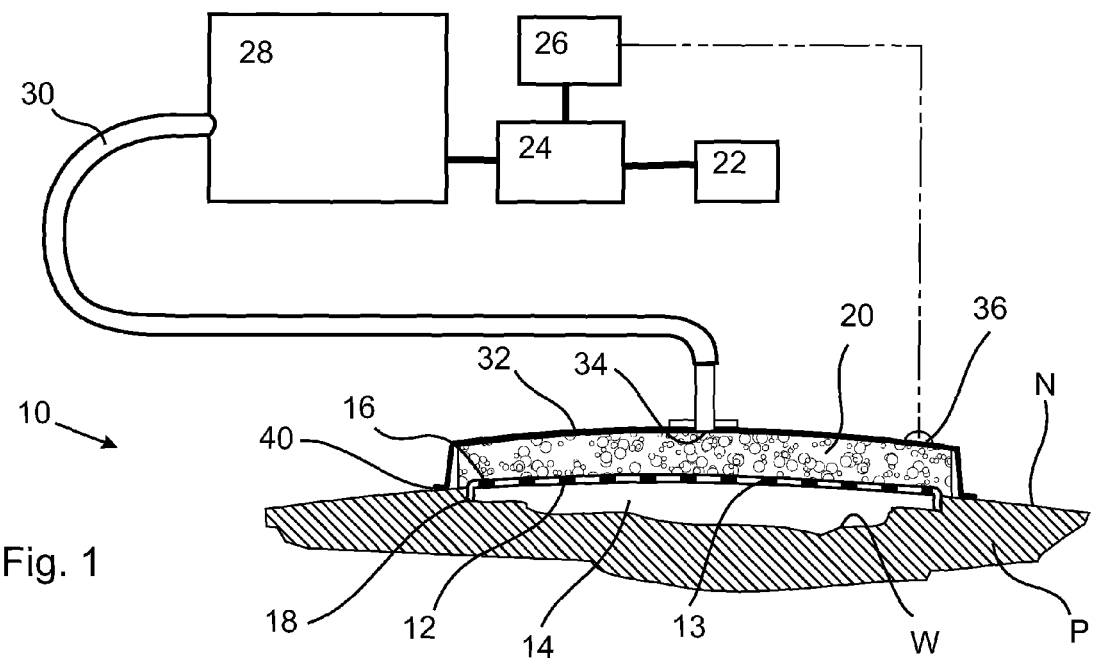
FIG. 1 is a schematic and part sectional view in accordance with the present invention.

Referring now to the drawings, a wound treatment apparatus of the present invention is generally designated by the numeral 10. The apparatus 10 can include a shaped tissue spacer 12 which can be made of a malleable metal or other shaped material such as rapidly formed plastic, such as that in stereolithography modeling using liquid UV-curable photopolymer "resin" and a UV laser to build parts a layer at a time. In this way the configuration of a void of tissue can be formed, herein referred to as the "projected growth tissue volume" 14, which in other words represents the tissue volume necessary to grow in order to make up the configuration of end shape desired.

Figure 2:
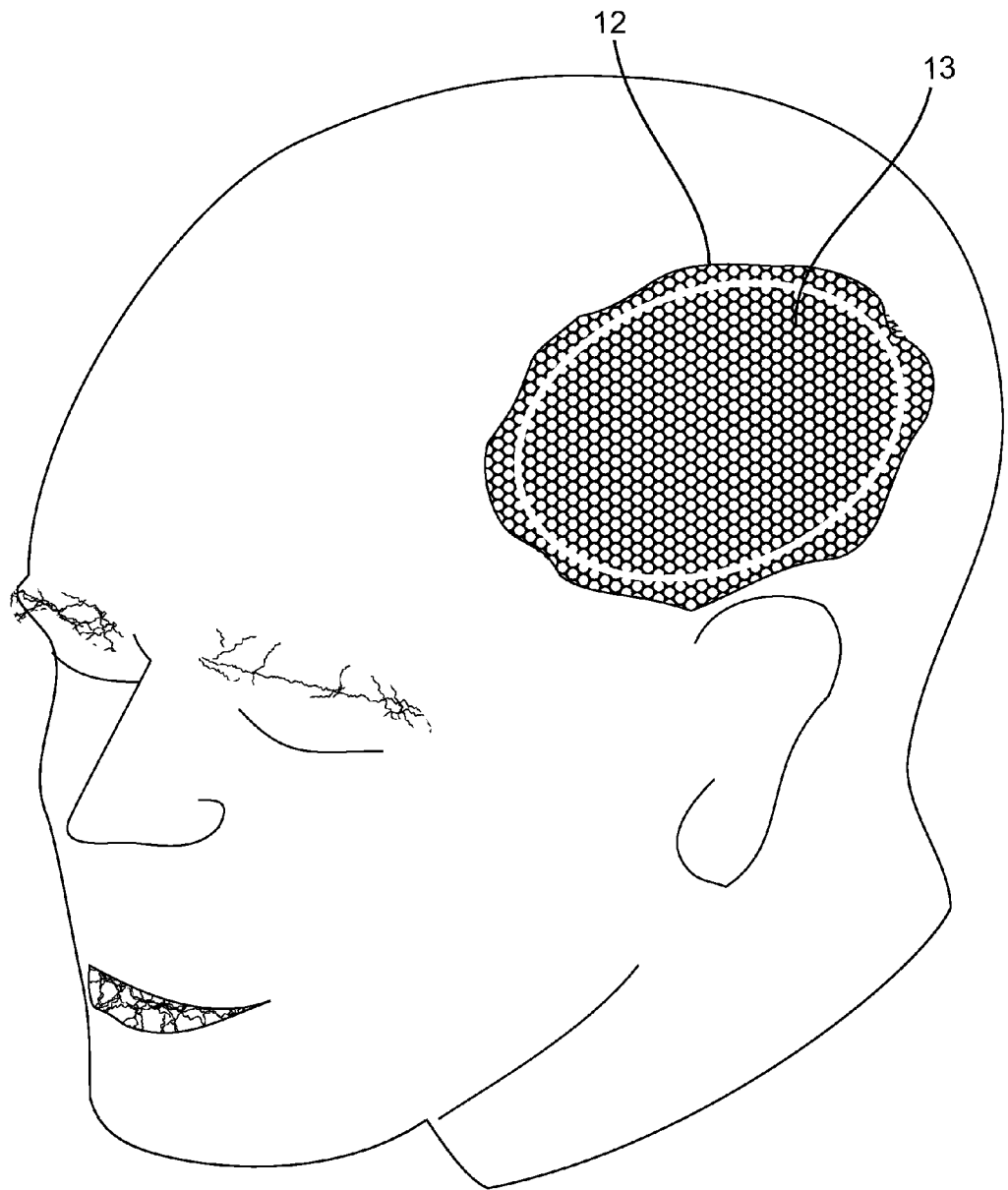
FIG. 2 is a perspective view of screen of the invention disposed in a wound.

The spacer 12 includes a plurality of opening surfaces 13 spatially positioned throughout the spacer 12 to permit fluid flow therethrough as readily seen in FIG. 2. The spacer 12 includes an outer surface 16 and peripheral edge 18. The edge 18 can preferably be of a length generally that of a depth of the wound W adjacent the point of insertion of the edge 18. The outer surface 16 can be of a configuration to generally span the wound W and form an outer barrier to which tissue growth will migrate and be generally bound. The outer surface 16 includes a contour which is shaped in accordance with a projected tissue shape complementary to the adjacent normal tissue N in order to place the patient condition better approximating original tissue configuration and shape.

Toward this end, a growth limiting material 20 such as a sponge or other open cell structure (e.g., open-cell polymer foam) can be employed on top of the spacer 12 to prevent tissue migration through open surfaces 13 yet permit air passage. Growth limiting material 20 may be used that vary in thickness and rigidity, although it may be desirable to use a spongy material for the patient's comfort if the patient must lie upon the appliance during treatment. The growth limiting material 20 can also be perforated to enhance gas flow and to reduce the weight of the apparatus. Thus, the growth limiting material 20 will aid in the removal of the spacer 12 by preventing growth of tissue over the outer surface 16.

In addition, the growth limiting material 20 serves to aid maintaining the position of the tissue spacer 12.

The spacer 12 can be formed by either crude hand formation using a malleable material, such as a suitable gauge metal screen, or can preferably be made by employing an imaging device 22 which can capture an image of the patient P and wound W and with the aid of a computer based device 24 having simulation software operably associated therewith can obtain the projected growth tissue volume 14 and then generate a predetermined spacer configuration data to be disposed in the projected growth tissue volume 14. The spacer configuration data can be used by a rapid making device 26 (which can be operably connected to the computer based device 24) in order to make the spacer 12 out of a polymer, for example.

Figure 3:
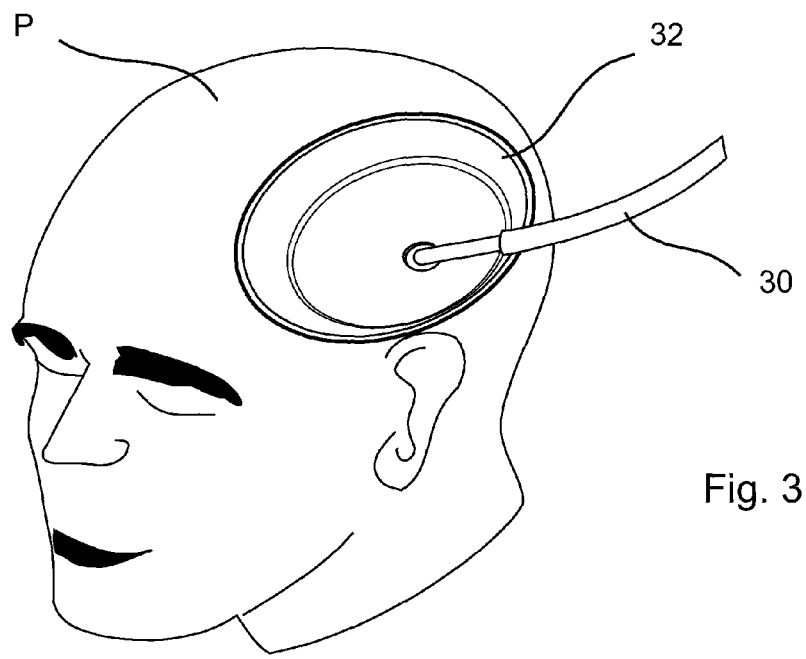
FIG. 3 is a schematic illustrating a reduced pressure appliance in accordance with the present invention in use over the spacer illustrated in FIG. 2.

A vacuum device 28 is provided for treating the wound W by application of reduced pressure (i.e., below atmospheric pressure) so that suction may be applied to the wound W preferably in a controlled manner for a selected time period. As schematically shown in FIGS. 1 and 3, vacuum device 28 is equipped with means to be applied to about the spacer 12, growth limiting material 20 and wound W to treat through the application of reduced pressure. The vacuum device 28 is preferably sealed in position over the spacer 12, growth limiting material 20 and the wound W to create a generally fluid-tight enclosure. In this regard, an adhesive material can be employed to adhere the vacuum device 28 to the skin surrounding the wound W.

The vacuum device 28 includes hollow suction tube 30 which connects to enclosure 32 to provide suction within the sealed enclosure 32. The suction tube 30 can be provided with a screen 34 to prevent the growth limiting material 20 from being inadvertently sucked into sealing engagement with the open end of the tube 30 thereby plugging and restricting flow.

The enclosure 32 can be secured and sealed to the surrounding normal skin N by an adhesive layer 40 to form a seal around the periphery of the wound W. The layer 40 can be an adhesive sheet such as Ioban, a product of the 3M corporation of Minneapolis, Minn.

The vacuum device 28 is understood to include a suction pump that produces a source of reduced pressure or suction which is supplied to the apparatus 10. As known in the art, a fluid trap, can be provided to remove and collect any exudate which may be aspirated from the wound W by the reduced pressure apparatus 10.

The computer based device 24 can be operably connected to the vacuum device 28 to control pressure differential in the enclosure 32 (i.e., the amount of suction or reduced pressure produced by the vacuum device 28). It is envisioned that a sensor 36 (e.g., a mechanical or electrical detection mechanisms) can be employed in the vacuum device 28 to sense a condition in the wound W. The computer based device 24 is operably connected to the sensor 36 in a manner to control the vacuum device 28 in accordance with the sensed condition. For example, if there a potential injurious situation exists such as when a blood vessel ruptures under during treatment and pressure differential can be adjusted accordingly.

Negative pressure appliances are useful for treating a variety of wounds. Treatment of a wound can be carried out by securing a negative pressure appliance to the treatment site as previously shown and described, and then maintaining a substantially continuous or cyclical reduced pressure within the apparatus 10 until the wound has reached a desired improved condition. A selected state of improved condition preferably includes formation of granulation tissue sufficient to fill the volume 14 to permit subsequent attachment of a graft.

The method is preferably practiced using a negative or reduced pressure ranging from 0.01 to 0.99 atmospheres, and more preferably practiced using a negative or reduced pressure ranging between 0.5 to 0.8 atmospheres. The time period for use of the method on a wound may preferably be at least 12 hours, but can be, for example, extended for one or more days. There is no upper limit beyond which use of the method is no longer beneficial; the method increases the rate of closure up to the time the wound actually closes. Satisfactory treatment of various types of wounds has been obtained via the use of reduced pressures equivalent to about 2 to 7 in. Hg below atmospheric pressure.

Supplying reduced pressure to the appliance in an intermittent or cyclic manner has also been demonstrated to be useful for treating wounds. Intermittent or cyclic supply of reduced pressure to an appliance may be achieved by manual or automatic control of the vacuum system. Optionally, implementation of artificial intelligence can be integrated into the computer based device 24 to determine what the optimum healing time is for the given condition. Such intelligence can include the use of neural networks.

A suitable vacuum system includes any suction pump capable of providing sufficient suction to the wound for medical purposes that is capable of providing the necessary suction. This can be learned via the neural network as well.

In conjunction with the present invention, known techniques of attachment of living tissue to a wound can be employed which include joining the living tissue to the wound to form a wound-tissue complex, then applying a negative or reduced pressure of selected magnitude to the wound-tissue complex over an area sufficient to promote migration of epithelia and subcutaneous tissue toward the complex, with the negative pressure being maintained for a selected time period sufficient to facilitate closure of the wound. Attachment of living tissue to a wound is a common procedure that can take many forms. For example, one common technique is the use of a "flap," a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure to the wound-graft complex reduces bacterial density in the complex and improves blood flow to the wound, thereby improving the attachment of the grafted tissue.

The terms and expressions which have been employed are used as terms of description and not of limitation and there is no intention in the use of such terms and expressions of excluding any equivalents of the features shown and described, or portions thereof, but it is recognized that various modifications are possible within the scope of the claimed invention. The claims appended hereto should therefore be deemed to cover such modifications, derivations and improvements.

What is claimed is:

1. An apparatus for administering a reduced pressure treatment to a projected tissue growth site of a patient, comprising: a tissue spacer including a shaped member having perforations therethrough and having an outer surface which generally confines about but does not substantially occupy a the void of a wound which is surrounded by generally normal dermis tissue of a patient and is configured to take a shape of a projected outer surface tissue which spans and connects surrounding generally normal dermis tissue of the patient and further characterized to include a contour complementary to the patient's surrounding generally normal dermis tissue and said shaped member having a peripheral edge extending laterally downward from said outer surface which is of a length configured to lay below the surrounding generally normal dermis tissue; and a reduced pressure supply device equipped for creating a pressure differential through said tissue spacer in a manner such that when said tissue spacer is disposed on the patient said device causes growth of tissue in a manner to conform with the shape of said contour of said tissue spacer and fill the void over time which further includes a porous growth limiting material disposed on said outer surface of said tissue spacer to limit tissue growth in a manner substantially beneath said outer surface.

2. The apparatus of claim 1, which further includes a computer based device operably connected to said reduced pressure device for controlling pressure differential to the tissue growth site.

3. The apparatus of claim 2, which further includes a sensor operably disposed adjacent the tissue growth site for sensing a condition thereof and operably connected to said computer based device such that said computer based device controls said reduced pressure device as a function of said condition.

4. The apparatus of claim 3, wherein said computer based device includes artificial intelligence to perform said control of reduced pressure device.

5. The apparatus of claim 1, wherein said tissue spacer is formed of one of metal and plastic.

6. A tissue spacer for treating a wound having a void, wherein the wound is surrounded by generally normal dermis tissue of the patient and the tissue spacer is readily shaped to confine a general configuration of a projected tissue growth site of a patient into the void for use in conjunction with vacuum suction for medical purposes, which comprises: a shaped member having perforations therethrough and having an outer surface which generally confines about but does not substantially occupy not the void of the wound and is configured to take a shape of a projected outer dermis surface tissue which spans and connects surrounding generally normal dermis tissue of the patient and further characterized to include a contour complementary to the patient's surrounding generally normal dermis tissue and said shaped member having a peripheral edge extending laterally downward from said outer surface which is of a length configured to lay below the surrounding generally normal dermis tissue.

7. The spacer of claim 1, which is formed of one of metal and plastic.

* * * * *